(12) United States Patent
Kriel et al.

(10) Patent No.: US 8,991,233 B2
(45) Date of Patent: Mar. 31, 2015

(54) ANALYSIS OF PRESSURIZED RESERVOIR FLUIDS

(75) Inventors: Wayne A. Kriel, Friendswood, TX (US); Graham M. Mullings, Magnolia, TX (US)

(73) Assignee: SGS North America Inc., Rutherford, NJ (US)

(*) Notice: Subject to any disclaimer, the term of this patent is extended or adjusted under 35 U.S.C. 154(b) by 176 days.

(21) Appl. No.: 13/455,688

(22) Filed: Apr. 25, 2012

(65) Prior Publication Data

US 2012/0272715 A1      Nov. 1, 2012

Related U.S. Application Data

(60) Provisional application No. 61/480,017, filed on Apr. 28, 2011.

(51) Int. Cl.
| | | |
|---|---|---|
| *G01N 30/04* | (2006.01) | |
| *G01N 30/12* | (2006.01) | |
| *G01N 30/88* | (2006.01) | |
| *G01N 33/24* | (2006.01) | |
| *G01N 33/28* | (2006.01) | |

(52) U.S. Cl.
CPC ............... *G01N 30/12* (2013.01); *G01N 30/88* (2013.01); *G01N 33/241* (2013.01); *G01N 33/2823* (2013.01); *G01N 2030/8854* (2013.01); *G01N 2030/8881* (2013.01)
USPC ........................................ 73/23.42

(58) Field of Classification Search
CPC ................................. G01N 2030/025
USPC ........................................ 73/23.42
See application file for complete search history.

(56) References Cited

U.S. PATENT DOCUMENTS 3,859,209 A * 1/1975 Jahnsen et al. ............. 210/664
4,409,814 A   10/1983 Onuma et al.

(Continued)

FOREIGN PATENT DOCUMENTS

| EP | 0092975 | 11/1983 |
|---|---|---|
| GB | 2292216 A | 2/1996 |

(Continued)

OTHER PUBLICATIONS

GPA Standard 2286-95, "Tentative Method of Extended Analysis for Natural Gas and Similar Gaseous Mixtures by Temperature Programmed Gas Chromatography," Gas Processors Association, 1999, 22 pages.

(Continued)

*Primary Examiner* — Hezron E Williams
*Assistant Examiner* — Rodney T Frank
(74) *Attorney, Agent, or Firm* — Fish & Richardson P.C.

(57) ABSTRACT

A self-contained analysis system operable to assess gas to oil ratio (GOR), shrinkage of reservoir fluid, and composition of pressurized reservoir fluids. The analysis system can be used for extended compositional analysis of rich flashed gas and lean gas samples as well as flashed equilibrium liquids, condensates, and black oils. Analysis of the various samples is achieved without cross contamination, for example, between rich flashed gases and lean gases or between extended natural gas and liquids (e.g., black oils and condensates). The system yields accurate results up to and including C20 for gas samples and up to and including C36+ for liquid samples, and entrained water.

15 Claims, 13 Drawing Sheets

(56) References Cited

U.S. PATENT DOCUMENTS

| | | | |
|---|---|---|---|
| 5,235,843 A | 8/1993 | Langhorst | |
| 5,400,657 A | 3/1995 | Kolpak et al. | |
| 5,499,531 A | 3/1996 | Henderson | |
| 5,889,202 A | 3/1999 | Alapati et al. | |
| 6,164,308 A | 12/2000 | Butler | |
| 6,865,926 B2 * | 3/2005 | O'Brien et al. | 73/23.27 |
| 6,872,571 B1 | 3/2005 | Adolfsen et al. | |
| 6,952,945 B2 * | 10/2005 | O'Brien | 73/23.35 |
| 7,257,987 B2 * | 8/2007 | O'Brien et al. | 73/23.41 |
| 7,467,540 B2 | 12/2008 | Kriel | |
| 7,621,171 B2 * | 11/2009 | O'Brien | 73/23.41 |
| 7,823,656 B1 | 11/2010 | Williams | |
| 8,347,688 B2 * | 1/2013 | O'Brien | 73/23.41 |
| 2003/0136185 A1 | 7/2003 | Dutten et al. | |
| 2005/0155906 A1 | 7/2005 | Wellington et al. | |
| 2007/0089483 A1 | 4/2007 | Kriel | |
| 2008/0141767 A1 | 6/2008 | Raghuraman et al. | |
| 2012/0011919 A1 | 1/2012 | Kriel | |

FOREIGN PATENT DOCUMENTS

| | | |
|---|---|---|
| RU | 2229122 C1 | 5/2004 |
| RU | 2404363 C2 | 11/2010 |
| WO | WO2007/041660 | 4/2007 |
| WO | WO2008064402 A1 | 6/2008 |
| WO | WO2012/012346 | 1/2012 |

OTHER PUBLICATIONS

GPA Standard 2186-02, "Method for the Extended Analysis of Hydrocarbon Liquid Mixtures Containing Nitrogen and Carbon Dioxide by Temperature Programmed Gas Chromatography," Gas Processors Association, 2002, 22 pages.

GPA Standard 2261-00, "Analysis for Natural Gas and Similar Gaseous Mixtures by Gas Chromatography," Gas Processors Association, 2000, 19 pages.

Kriel et al.; "Improved Gas Chromatographic Analysis of Reservoir Gas and Condensate Samples"; Proceedings of the 1993 SPE International Symposium on Oilfield Chemistry; New Orleans, Louisiana, USA; Mar. 2-5, 1993; pp. 397-411.

Authorized Officer A. Witzig. International Search Report and Written Opinion in International Application No. PCT/US2006/038905 Jan. 18, 2007, 14 pages.

Authorized Officer M. Bravin. International Preliminary Report on Patentability in International Application No. PCT/US2006/038905, Jan. 16, 2008, 15 pages.

Authorized Officer M. Conner. International Search Report and Written Opinion in International Application No. PCT/US2011/044396, Sep. 29, 2011, 11 pages.

International Preliminary Report for International Application No. PCT/US2011/044396, dated Nov. 8, 2012, 8 pages.

Witten Opinion for International Application No. PCT/US2012/035445, dated May 31, 2013, 6 pages.

International Preliminary Report on Patentability for International Application No. PCT/US2012/035445, dated Jul. 9, 2013, 7 pages.

Burke et al; Extended Analysis of Live Reservoir Oils by Gas Chromatography; SPE International Symposium on Oilfield Chemistry; 1991; pp. 79-86.

International Search Report; Witzig; Jul. 25, 2012; World Intellectual Property Organization (WIPO) (International Bureau of); PCT/US2012/035445; 15 pages.

Written Opinion of the International Preliminary Examining Authority; Aug. 9, 2012; World Intellectual Property Organization (WIPO) (International Bureau of); PCT/US2011/044396; 6 pages.

\* cited by examiner

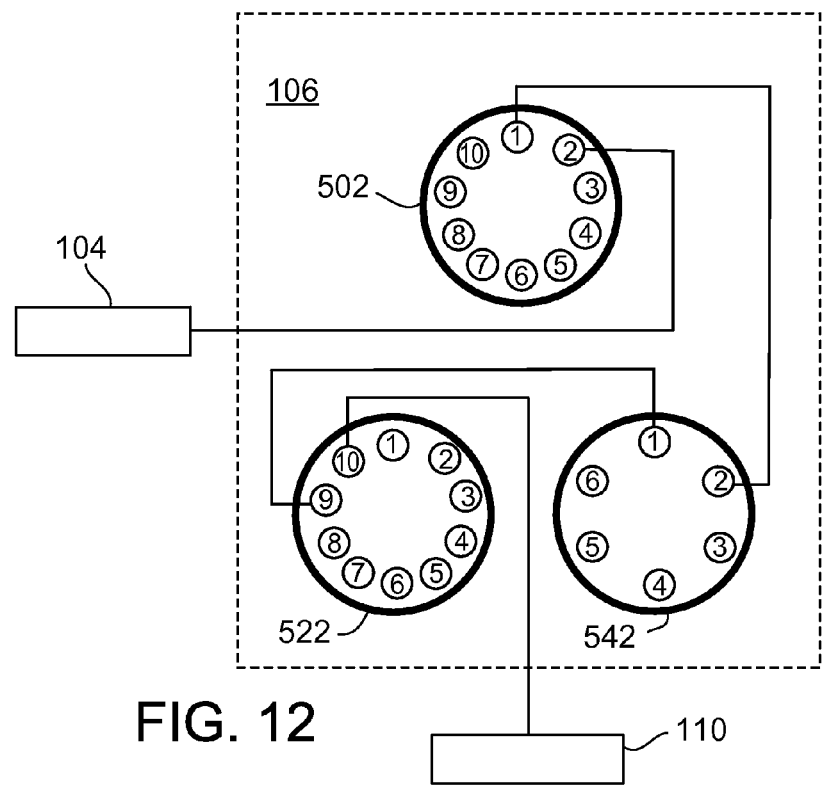
FIG. 12
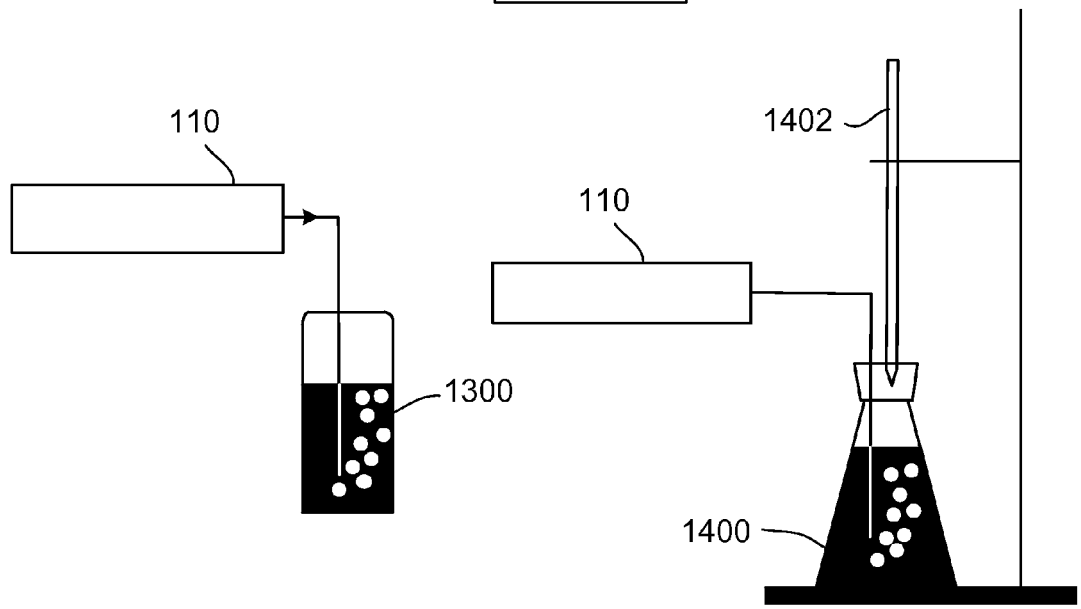
FIG. 13
FIG. 14

ANALYSIS OF PRESSURIZED RESERVOIR FLUIDS

CROSS-REFERENCE TO RELATED APPLICATION

This application claims priority to U.S. application Ser. No. 61/480,017 filed on Apr. 28, 2011, entitled "Analysis of Pressurized Reservoir Fluids," which is incorporated by reference herein in its entirety.

TECHNICAL FIELD

This disclosure relates to a system for analysis of reservoir fluids such as live (pressurized) crude oil.

BACKGROUND

There are instances where it is desired to determine the composition of a reservoir fluid for reservoir management purposes, such as to determine gas to oil ratios, fluid shrinkage, and extended composition. These fluids typically exist or are produced at elevated pressures and temperatures. Although some offshore platforms maintain a small laboratory for determination of basic fluid properties, space on the platform may not permit the equipment necessary to analyze the fluid in detail. Therefore, a sample taken on an offshore platform may be transported to an onshore testing facility. In some cases, it is not practical to maintain the voluminous analysis equipment at remote sampling sites, such as deep water offshore platforms, remote locations, underdeveloped countries, and rural areas. Depending on the location of the offshore platform or rural onshore sampling site, the sample may travel hundreds or thousands of miles to reach the testing facility. This travel can introduce a considerable lag between the time the sample is taken and the time the analysis is performed. This time lag discourages frequent testing and can reduce or sometimes eliminate retesting. The travel increases the likelihood that the sample will become compromised and/or contaminated, and introduces additional expenses related to travel and time into the costs of analysis. If a sample is contaminated or fouled during collection, transport, or otherwise, the contamination or fouling may not be discovered until the sample has traveled the many miles to reach the centralized testing facility. In such cases, when possible, another sample is then taken and transported to the centralized testing facility.

In some cases, the headspace vapor from a liquid, rather than the liquid itself, may be analyzed in a laboratory on an offshore platform. While this approach allows analysis at the site, the analysis may provide less information than desirable. Furthermore, when analysis of reservoir fluids includes flash vaporization, a separate apparatus may be required to flash the sample and collect the liquid and vapor phases, in which case the liquid and vapor phases are typically transferred to another apparatus for compositional analysis.

SUMMARY

In one aspect, an analysis system for pressurized reservoir fluid includes a housing having a first chromatography subsystem, a second chromatography subsystem, and a flash apparatus. The flash apparatus partially vaporizes the pressurized reservoir fluid to yield a vaporized gas and a reservoir liquid. The vaporized gas flows within the housing from the flash apparatus to the second chromatography subsystem via the first chromatography subsystem, and the first and second chromatography subsystems are actuated simultaneously or substantially simultaneously to detect components in the reservoir fluid.

Implementations include one or more of the following features. In some cases, the first chromatography subsystem is configured to detect fixed gases. The second chromatography subsystem can be configured to detect C1 to C5 hydrocarbons. In certain cases, the first chromatography subsystem includes a first thermal conductivity detector, and the second chromatography subsystem includes a second thermal conductivity detector. The housing may further include a third chromatography subsystem configured to detect C1 to C20 hydrocarbons. In an example, the third chromatography subsystem includes a flame ionization detector.

The analysis system may include a gas analytical capillary column, a liquid analytical capillary column, and a selector valve. The gas analytical capillary column and the liquid analytical capillary column may be coupled to the flame ionization detector via the selector valve. In some cases, the third chromatography subsystem includes the gas analytical capillary column. The analysis system may further include a conduit configured to transport the vaporized gas from the flash apparatus to the first chromatography subsystem. A temperature of the conduit can be controlled using available heat in the analysis system.

In some implementations, the analysis system includes a single data acquisition system coupled to the first chromatography subsystem, the second chromatography subsystem, and the flash apparatus. The single data acquisition system may be configured to acquire data related to the composition of the vaporized gas and the reservoir liquid. The analysis system may also include a microprocessor coupled to the data acquisition system, wherein the microprocessor is operable to assess a gas to oil ratio of the pressurized reservoir fluid based on data acquired by the data acquisition system.

In certain implementations, the flash apparatus partially vaporizes the pressurized reservoir fluid to yield free water along with the vaporized gas and the reservoir liquid. The reservoir liquid may be an equilibrated reservoir liquid. The analysis system is an integrated or self-contained unit.

Another aspect includes partially vaporizing a pressurized reservoir fluid to form a vaporized gas and a reservoir liquid, automatically providing a single sample of the vaporized gas to two chromatography subsystems in series, acquiring data related to the composition of the vaporized gas from the two chromatography subsystems with a single data acquisition system, and quantifying the composition of the reservoir liquid based on data acquired by the single data acquisition system.

Implementations may include one or more of the following features. In some cases, the single sample of the vaporized gas is automatically provided to a third chromatography subsystem in series with the two chromatography subsystems. In certain cases, the reservoir liquid is provided to a third chromatography subsystem. Data related to the composition of the reservoir liquid from the third chromatography subsystem may be acquired with the single data acquisition system, the data related to the composition of the reservoir liquid and the data related to the composition of the vaporized gas may be combined, and the composition of the pressurized reservoir fluid based on data acquired by the single data acquisition system may be quantified.

In some cases, condensation of the vaporized gas may be inhibited before automatically providing the single sample of the vaporized gas to the two chromatography subsystems in series. Inhibiting condensation may include, for example, heating the vaporized gas with available heat. In certain cases, a weight ratio of the vaporized gas to the reservoir liquid may be assessed.

Features of the systems and methods described herein allow automated analysis of a sample of pressurized reservoir fluid without handling of the sample during the analysis process. The self-contained nature of the analysis system described herein allows characterization of a pressurized reservoir fluid by an integrated approach such that a portion of the sample is not transferred from an interior of the analysis system to another system or subsystem outside the housing of the analysis system. Advantages include reduction in sample losses and operator-induced error. In addition, condensation of heavy hydrocarbons is inhibited.

These general and specific aspects may be implemented using a device, system or method, or any combination of devices, systems, or methods. The details of one or more embodiments are set forth in the accompanying drawings and the description below. Other features, objects, and advantages will be apparent from the description and drawings, and from the claims.

BRIEF DESCRIPTION OF THE DRAWINGS

The concepts herein may be more completely understood in consideration of the following detailed description of various embodiments in connection with the accompanying drawings, in which:

FIG. 12 depicts a valve series schematic for sample injection;
FIG. 13 depicts an apparatus for scrubbing vent gas;
and
FIG. 14 depicts an apparatus for titrating vent gas.

DETAILED DESCRIPTION

The analysis system described herein is a self-contained unit operable to assess gas to oil ratio (GOR) and fluid shrinkage of reservoir fluids, and can be used for extended compositional analysis of rich flashed gas and lean gas samples as well as flashed equilibrium liquids, condensates, and black oils. Analysis of the various samples is achieved without cross contamination, for example, between rich flashed gases and lean gases or between extended natural gas and liquids (e.g., black oils and condensates). The system can yield accurate results up to and including C20 for gas samples and up to and including C35 for liquid samples. In the case of liquids, components greater than C35 are determined by mass balance and are considered to be a single component referred to as C36+.

Figure 1A:
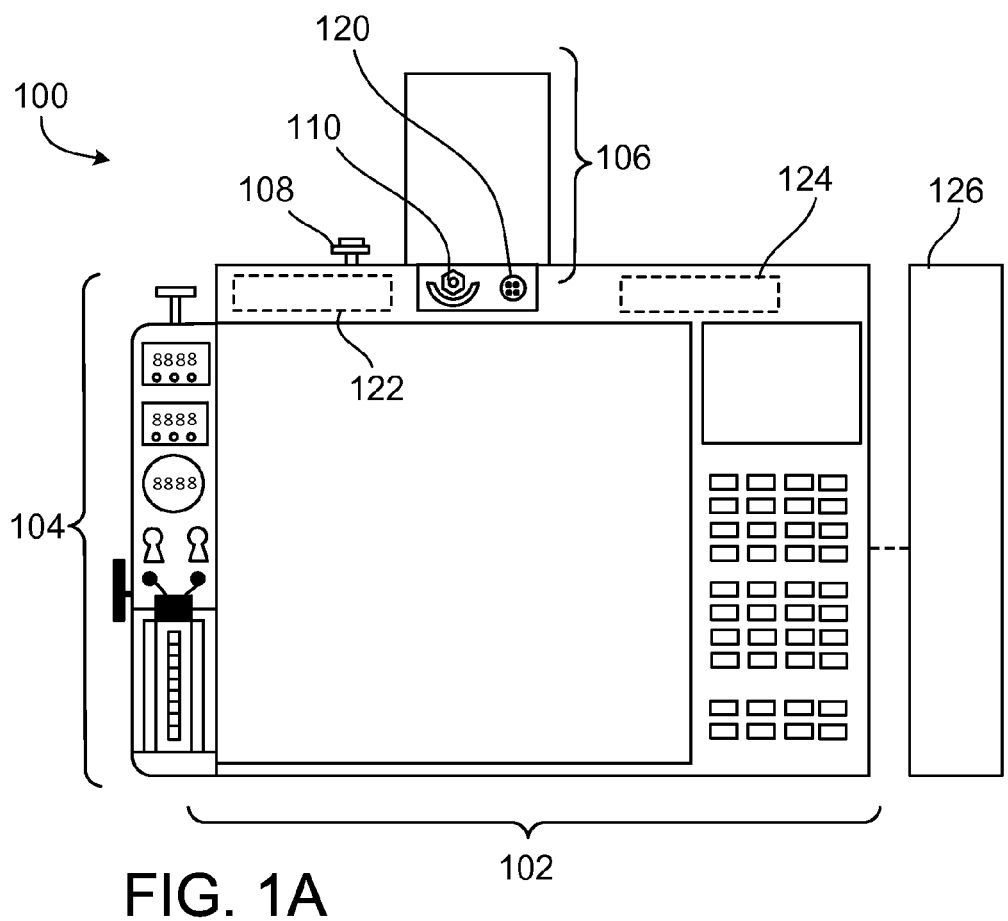
FIG. 1A is a front view of an analysis system.
Figure 1B:
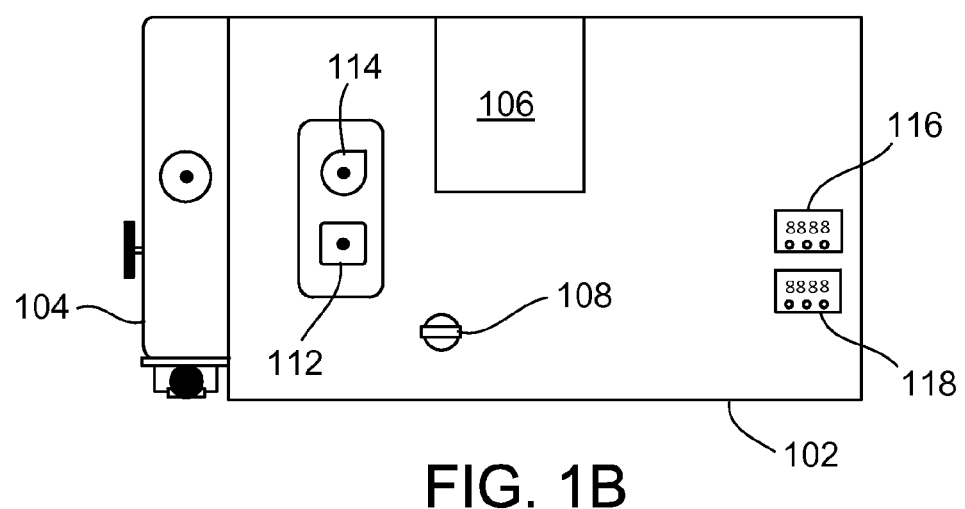
FIG. 1B is a top view of the analysis system depicted in FIG. 1A.

FIGS. 1A and 1B show front and top views, respectively, of analysis system 100. Analysis system 100 includes gas chromatograph 102, flash apparatus 104, and isothermal oven 106. Analysis system 100 is a device capable of accepting a sample of pressurized reservoir fluid and analyzing composition and other characteristics of the fluid (e.g., of two or more phases of the fluid) without transferring the sample fluid or a portion of the sample fluid (e.g., a vapor component) from an interior of the device to another system (e.g., a subsystem) exterior to (e.g., and coupled to) the device. Analysis system 100 is a single, compact unit that can be shipped to an offshore platform in one crate, unpacked, and placed in a laboratory on the platform for immediate analysis of live fluids. Assembly or concatenation of additional units is not required for full compositional analysis of a reservoir fluid at the platform.

Gas chromatograph 102, flash apparatus 104, and isothermal oven 106 are integrated in a common housing, such that gas samples move internally (i.e., within the housing) between the flash apparatus and the isothermal oven, between the isothermal oven and the gas chromatograph, etc. in a thermally controlled environment without exiting analysis system 100. Available heat inside analysis system 100 (e.g., heat generated by gas chromatograph 102, isothermal oven 106, etc.) is used for heating of the gas lines that transfer gas between the flash apparatus and the isothermal oven, between the isothermal oven and the gas chromatograph, etc. such that condensation of the gas, or components of the gas, is avoided. For example, an external power supply, heat tape, etc. is not needed to inhibit condensation of the gas or components of the gas.

Analytical column selector 108 is coupled to a valve inside analysis system 100 and allows the user or programmer to select (e.g., remotely and/or automatically) between a gas analytical capillary column and a liquid analytical capillary column housed in gas chromatograph 102 for analysis of gas and liquid samples, respectively. Isothermal oven 106 includes three analytical subsystems, one of which is coupled to the gas analytical capillary column, and all of which are linked to allow sample loops in the subsystems to be filled in series with a sample from flash apparatus 104 or a sample injected through gas inlet/outlet 110 when the gas analytical column in gas chromatograph 102 is selected. When the liquid analytical column is selected, a liquid sample injected through back inlet 114 enters the liquid analytical column in gas chromatograph 102. Analysis system 100 also includes temperature controllers 116 and 118. Temperature controller 116 controls the temperature of isothermal oven 106, and temperature controller 118 controls the temperature of the gas transfer line external to analysis system 100 to inhibit condensation of heavier components in the transfer line.

Data from analysis system 100 (e.g., from gas chromatograph 102 and flash apparatus 104) are acquired by a single, common data acquisition system 122 and are manipulated by microprocessor 124. In certain embodiments, analysis system 100 communicates with computing device 126 (e.g., a personal computer) to enable viewing, analysis and manipulation of the data output from the reservoir fluid analysis system. In certain embodiments, computing device 126 is linked to a network that allows remote computing devices to communicate with computing device 126 and in some instances remotely operate analysis system 100. In certain embodiments, computing device 126 can enable a remote party to communicate with an operator to provide the operator instruction on operating analysis system 100.

Figure 2A:
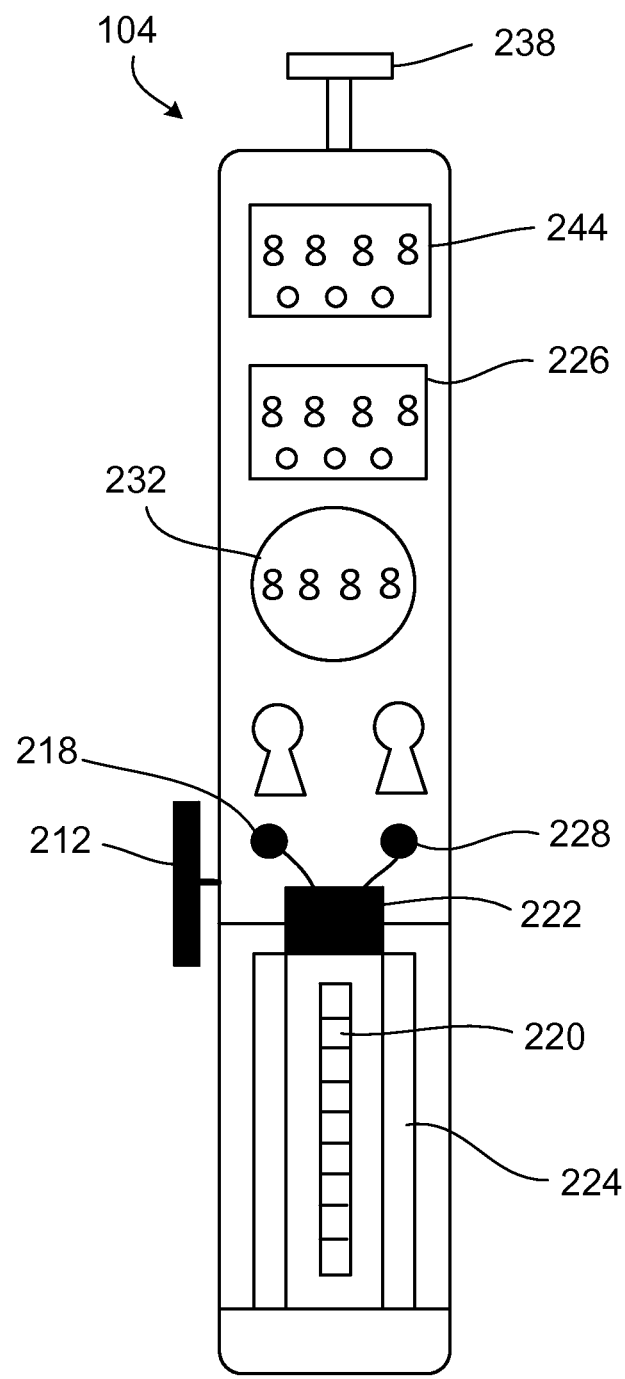
FIG. 2A is a front view of a flash apparatus.
Figure 2B:
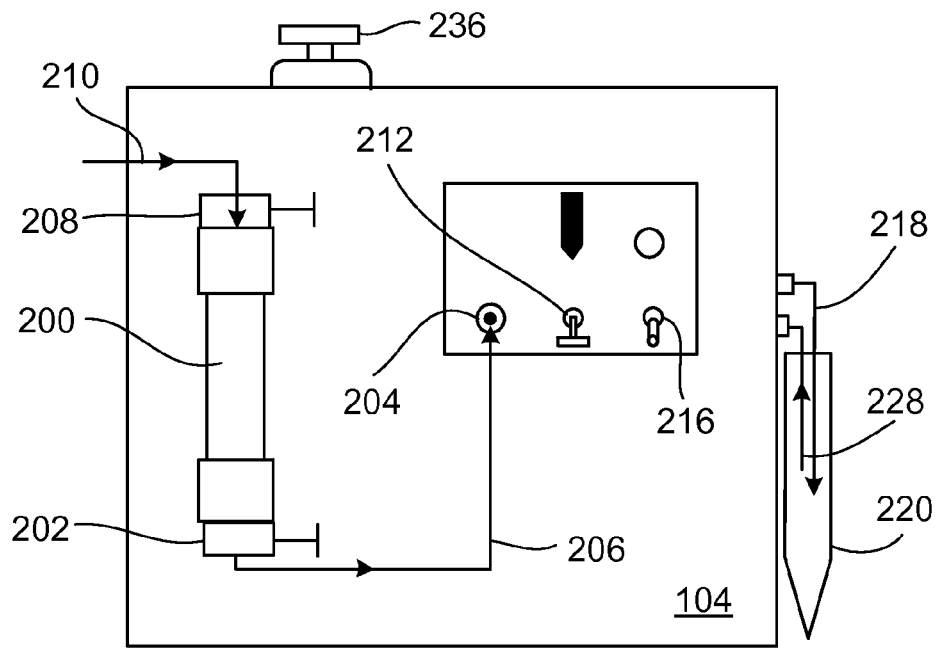
FIG. 2B is a side view of the flash apparatus of FIG. 2A.
Figure 2C:
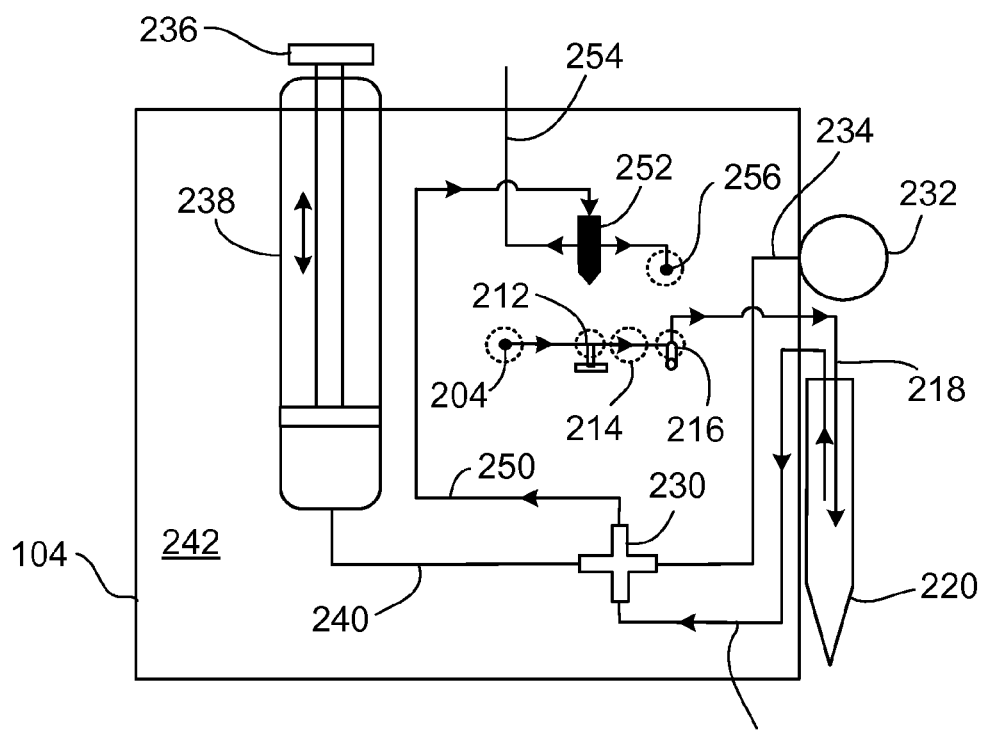
FIG. 2C is an internal view of the flash apparatus of FIG. 2A.

Flash apparatus 104 is a single stage flash apparatus that allows for samples to be flashed to atmospheric conditions with isolation, collection, and measurement of the liberated phases (i.e., gas, oil, and water). Isolation and measurements of the respective phases allows for the determination of the gas to oil ratio (GOR), fluid shrinkage, and gas and liquid compositions, as well as the calculation of live density from mass balance. FIGS. 2A, 2B, and 2C show front, side, and internal views of flash apparatus 104, respectively.

Pycnometer 200 containing a pressurized sample fluid is coupled through valve 202 to inlet 204 of flash apparatus 104 by line 206. Pycnometer 200 may be removed from the flash apparatus 104 and transported to collect the fluid sample. In an example, pycnometer 200 is carried by an operator from flash apparatus 104 to a location where the sample will be collected, the sample collected, and pycnometer 200 returned to flash apparatus 104. This eliminates the need to transfer the fluid sample between multiple vessels, such as between the location where the sample is collected and an intermediate sample vessel and from an intermediate sample vessel and pycnometer 200. In other embodiments, pycnometer 200 remains connected to flash apparatus 104 throughout operation, and sample fluid is collected and deposited in the pycnometer, for example, via an intermediate sample vessel.

Pycnometer 200 internally defines an elongate cavity that sealingly receives a piston. The piston divides the elongate cavity into two distinct chambers: a drive fluid (pressurized liquid or gas) chamber and a sample chamber. The sample chamber is operable to receive the fluid sample through valve 202. After receiving the fluid sample, the valve 202 is closed to retain the fluid sample in the sample chamber. The maximum volume of pycnometer 200 is precisely calibrated for pressure and temperature. Additionally, the "dry" weight of pycnometer 200 is precisely known. The volume of the fluid sample, thus, can be determined by adjusting the maximum volume of the sample chamber for the temperature and pressure of the fluid sample therein. The weight of the fluid sample can be determined by weighing pycnometer 200 containing the fluid sample and subtracting the dry weight of the pycnometer. The density of the fluid sample can be determined by dividing the determined weight by the determined volume.

The size of pycnometer 200 can be selected to facilitate handling by the operator. A smaller vessel is more easily manipulated and carried by the operator. In one instance, pycnometer 200 has an internal volume of approximately 10 cc when calibrated at 1000 psi and 20° C. and is constructed from 316 stainless steel. To facilitate removal and return of pycnometer 200 to flash apparatus 104, an outlet of pycnometer 200 may be coupled to a quick release connection that allows easy installation and removal of the pycnometer from the remainder of flash apparatus 104. In certain embodiments, low dead volume fittings are used in one or more locations of flash apparatus 104, for example, the connections with pycnometer 200.

As noted above, pycnometer 200 includes a piston that divides the elongate cavity into a drive fluid chamber and a sample chamber. Pycnometer 200 may further include valve 208 provided in communication with a drive fluid chamber. With valve 208 open, fluid from the drive fluid chamber flows into pycnometer 200 through valve 208 via line 210. Receiving the fluid sample in the sample chamber drives the piston in the elongate cavity to expand the sample chamber and reduce the drive fluid chamber. A drive fluid may be introduced through valve 208 to pressurize the drive fluid chamber. Pressure in the drive fluid chamber exerts pressure, via the piston, on the fluid sample in the sample chamber. When valve 202 is opened, the pressure in the sample chamber drops. Pressure in the drive fluid chamber drives the piston to reduce the sample chamber and drive the fluid sample out of pycnometer 200. In some instances, for example where the fluid sample is live crude under pressure, the fluid sample may separate into two phases (i.e., vapor and liquid) when valve 202 is opened and pressure within the sample chamber drops. The heavier liquid phase of the fluid sample then accumulates about the bottom of the sample chamber, and the vapor phase of the fluid sample rises to the top of the sample chamber. Movement of the piston expels the vapor and liquid phases of the fluid sample through line 206 and into inlet 204.

The drive fluid may be sourced from a number of different sources. In an example, the drive fluid is pressurized gas stored in a canister. The outlet of the canister may be sized or a restriction may be provided about the outlet of the canister to meter the flow from the canister. In certain embodiments, the canister is a standard 12-gram $CO_2$ cartridge, such as those used with $CO_2$ powered guns. The standard 12-gram $CO_2$ cartridge can apply approximately 1000 psig driving pressure to the drive fluid chamber. In other examples, the fluid sample may be evacuated from the sample chamber in other manners. For example, a mechanical or electromechanical system, such as a motor and a gear train or screw drive, may be used to move the piston.

The pressurized gas or in some cases a mechanical drive forces fluid (i.e., gas and liquid) from pycnometer 200 through needle valve 212. The reduction in pressure across needle valve 212 causes the fluid to undergo a partial vaporization referred to as flash vaporization. Flashing occurs in flash station 214 between needle valve 212 and metering valve 216. In some cases, flash station 214 is backlit to allow observation of foaming, emulsions, and other operating issues in the flash station 214. Metering valve 216 controls the flow rate of fluid in line 218 to receiver 220.

Receiver 220 has gas-tight seal 222 and is housed in chamber 224. The temperature in chamber 224 is controlled by temperature controller 226 for example, to maintain the contents of receiver 200 at a constant or substantially constant temperature. In some cases, temperature controller 226 is coupled to a heating element or a cooling element. Receiver 220 can be cooled by a cooling element 35 to facilitate and/or increase condensation of liquid in the receiver. In an example, temperature controller is coupled to a Peltier effect device configured to carry (e.g., by aluminum holder) and conductively transfer heat with receiver 220. In other embodiments, the cooling element includes an electrical cooler, a chemical cooler, or another device configured for one or more modes of heat transfer.

In certain embodiments, receiver 220 includes graduations that enable visual determination of the volume collected in the receiver. The "dry" weight of receiver 200 prior to receipt of the liquid phase may be precisely measured. The weight of the liquid phase can then be determined by measuring the weight of receiver 220 after receipt of the liquid phase and subtracting the dry weight of the receiver. The density of the liquid phase can be determined via a densitometer. The volume of the liquid phase collected in receiver 200 can be determined with reference to the graduation or by dividing the weight of the liquid phase in the receiver by the density determined via the densitometer. In an example where the fluid sample includes live crude, the volumetric shrink can be determined by comparing the volume of liquid phase contained in receiver 220 to the maximum volume, adjusted for pressure and temperature, of the fluid sample in pycnometer 200.

In certain embodiments, receiver 220 is a centrifuge tube that can be removed from flash apparatus 104 and directly, without transferring the fluid to another vessel, inserted into a centrifuge device. In an example where the fluid sample is live crude, the liquid phase may include oil, water, and entrained solids. Centrifuging the liquid phase separates the oil, water, and solids and enables measurement, for example visually using the graduations, of the volume of oil, water, and solids. The volume and weight of liquid phase in receiver 220 can be corrected for water and sediment recovered during the centrifuging process without the need of taking another fluid sample.

Gas from receiver 220 flows via line 228 to four-way splitter 230. Flash apparatus 104 is equipped with digital pressure gauge 232 to monitor internal pressure of the system via line 234 from four-way splitter 230. The internal pressure of the system can be adjusted to atmospheric pressure by movement of a rod attached to piston 236 of gasometer 238 as vapor from receiver 220 flows via line 240 to the gasometer. Vapor from gasometer 238 operates to measure the amount of the vapor phase collected. In certain embodiments, gasometer 238 is a floating piston gas meter having a graduated cylinder that sealingly receives piston 236. In some instances, piston 236 can additionally or alternatively be coupled to a graduated shaft (e.g. a plunger handle) extending from gasometer 238. Receipt of the vapor phase in the graduated cylinder displaces piston 236, and the volume of the vapor phase can be visually determined from the graduations on gasometer 238 (or on the shaft, if so provided). In some cases, the cylinder is purged prior to receipt of the vapor phase to ensure an accurate measurement. Gasometer 238 may include an internal mixer (e.g., a magnetic mixer) operated, for example, during or at the end of each vapor collection cycle to ensure that the vapor containing the gas meter is well mixed and of a uniform composition.

Gasometer 238 is housed in enclosure 242. The temperature of gasometer 238 is controlled by temperature controller 244 (e.g., coupled to a heating element) to maintain the contents of gasometer 238 at a constant or substantially constant temperature. The temperature and pressure of the vapor in gasometer 238 are monitored, so that the volume determined with the gasometer can be corrected to standard conditions. In an example, gasometer 238 is heated to (or is held at) a temperature of about 50° C. (120° F.).

The density of the gas collected in gasometer 238 is calculated from its composition in accordance with GPA 2286 ("Tentative Method of Extended Analysis for Natural Gas and Similar Gaseous Mixtures by Temperature Programmed Gas Chromatography," Revised 1995, Gas Processors Association), which is incorporated herein by reference. The gas to oil ratio (GOR) is calculated from the volume ratio of the gas (collected in gasometer 238) to the liquid (collected in receiver 220) at 15.6° C. (60° F.).

An insulative barrier may be provided to thermally isolate or substantially thermally isolate a portion of flash apparatus 104 from another portion of the flash apparatus. In certain embodiments, receiver 220 and four-way splitter 230 are thermally isolated from gasometer 238 to reduce communication of heat output from a heating or cooling element to the liquid phase of the sample.

The vapor phase of the fluid sample travels from four-way splitter 230 via line 250 to valve 252. As depicted, valve 252 is a three-way selector valve used to direct the flow of gas in flash apparatus 104. When valve 252 is in position I, gas from flash apparatus 104 flows internally (i.e., inside analysis system 100) to gas chromatograph 102 via line 254. When valve 252 is in position II, the valve is closed and gas is contained in flash apparatus 104. When valve 252 is in position III, excess gas exits flash apparatus 104 through vent 256 (e.g., after a gas sample has been analyzed). In some cases, vent 256 is fitted so that a ⅟₁₆" line of plastic tubing can be used to run excess gas through a scrubbing solution (e.g., as depicted in FIG. 13) when samples contain harmful or foul-smelling components.

Flash apparatus 104 may be purged with carrier gas (e.g., before flashing a sample) by connecting a carrier gas source to inlet 204. With the needle valve of the carrier gas line open, needle valve 212 and metering valve 216 are opened. Valve 252 is turned to position I, and analysis system 100 is purged. Once analysis system 100 is purged, valve 252 is closed, metering valve 216 is closed, and needle valve 212 is closed, respectively, to ensure that carrier gas remains in the system. The carrier gas line is then removed from inlet 204, and pycnometer 200, filled with a single phase pressurized fluid, is coupled to the inlet.

The composition of the fluid sample loaded in the pycnometer can be calculated from extended composition of each equilibrium phase (gas, hydrocarbon liquid) as assessed by gas chromatograph 102 and mathematical recombination of the respective phases. Gas from gasometer 238 can be provided to gas chromatograph 102 through line 254 with valve 252 in position I. Liquid from receiver 220 of flash apparatus 104 can be provided to gas chromatograph 102 through back inlet 114. The injection of the sample can be accomplished by hand or with the use of an automatic sampler. An example of a suitable automatic sampler is the Agilent GC Autosampler Model 7673, available from Agilent Technologies, Inc. (Santa Clara, Calif.).

Figure 3:
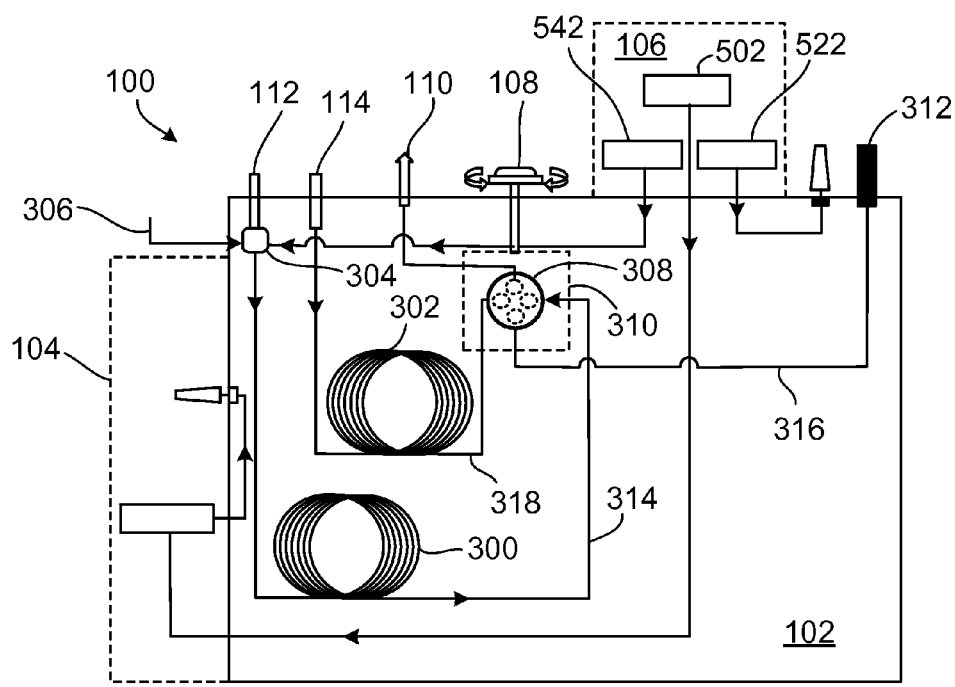
FIG. 3 is an internal view of the analysis system depicted in FIGS. 1A and 1B.

FIG. 3 is an internal view of analysis system 100. In an example, gas chromatograph 102 is the Agilent 7890 GC, available from Agilent Technologies, Inc., modified as described herein to switch between two dedicated analytical columns: one for gas (e.g., from gasometer 238 of flash apparatus 104) and one for liquids (e.g., from receiver 220 of flash apparatus 104). As depicted in FIG. 3, gas chromatograph 102 includes gas analytical column 300 (e.g., a capillary nonpolar boiling point column) coupled to front inlet 112 and liquid analytical column 302 (e.g., a capillary nonpolar boiling point column) coupled to back inlet 114. Front inlet 112 is coupled to splitter 304, and can be used in a split or splitless mode. In an example, front inlet 112 is operated in a split mode with a split of 5 parts carrier gas to 1 part sample. A sample provided to front inlet 112 flows to gas analytical column 300. The sample may be, for example, a sample from a gas cylinder, such as a calibration standard. A carrier gas (e.g., hydrogen or helium) may be provided to splitter 304 through line 306 to force the sample through gas analytical column 300 or to flush the gas analytical column after a sample has been run.

Gas analytical column 300 and liquid analytical column 302 are both coupled to valve 308. As depicted, valve 308 is a four-port valve available from Valco Instruments Co. Inc., (Houston, Tex.). Analytical column selector 108 is also coupled to valve 308. Analytical column selector 108 operates valve 308 in valve unit 310 to selectively couple gas analytical column 300 or liquid analytical column 302 to flame ionization detector 312. When gas analytical column 300 is selected, line 314 from gas analytical column 300 is coupled to line 316, and line 318 from liquid analytical column 302 is coupled to line 320, such that the sample from gas analytical column 300 flows to flame ionization detector 312, and liquid analytical column 302 is vented to gas inlet/outlet 110. When liquid analytical column 302 is selected, line 318 from liquid analytical column 302 is coupled to line 316, and line 314 from gas analytical column 300 is coupled to line 320, such that the sample from liquid analytical column 302 flows to flame ionization detector 312, and gas analytical column 300 is vented to gas inlet/outlet 110.

Figure 4:
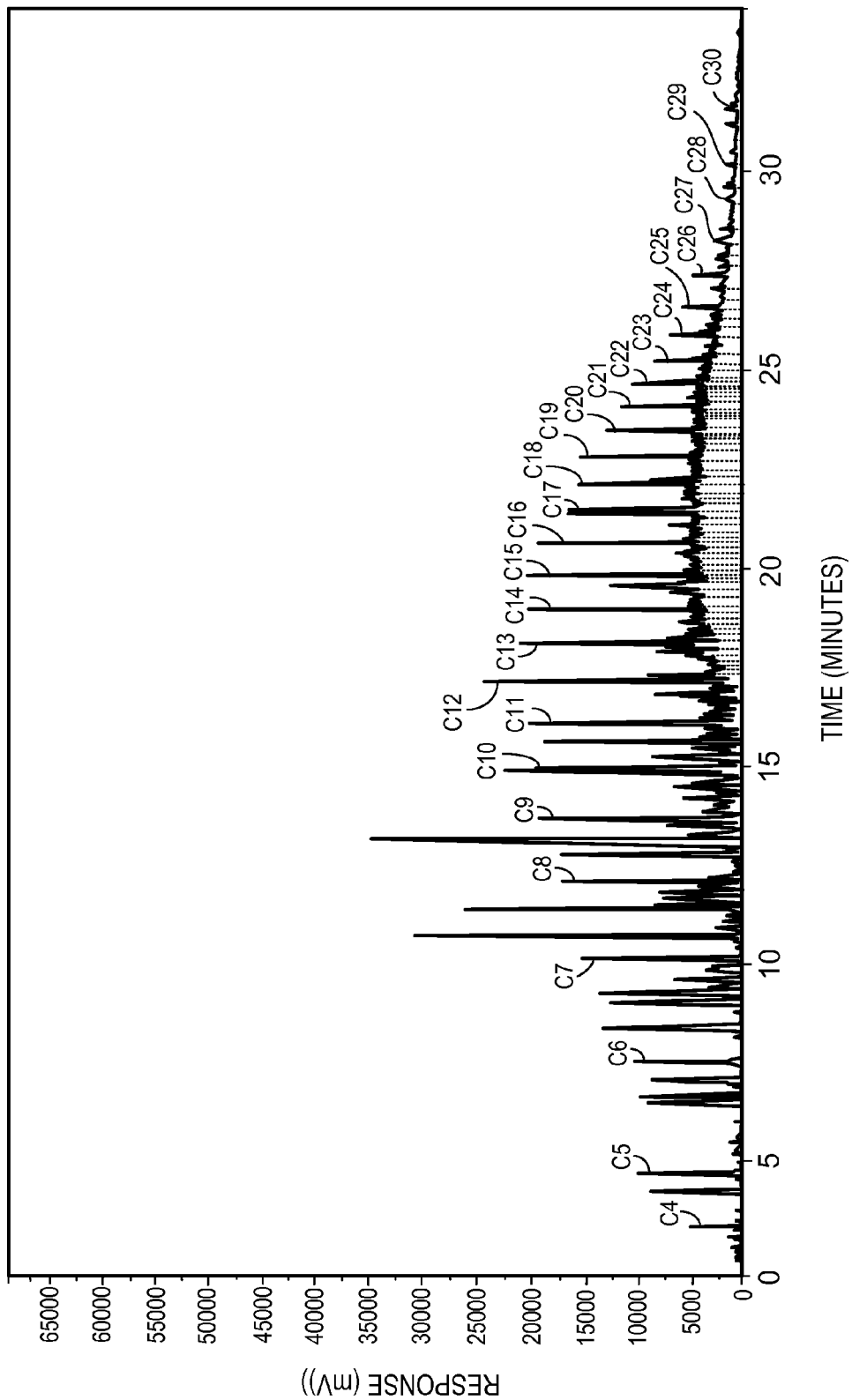
FIG. 4 depicts a sample chromatograph from an equilibrium liquid sample.

Back inlet 114 is a temperature programmed, on-column inlet used for the analysis of hydrocarbon liquids ranging from light condensates to heavy black oils. Before running a liquid sample, sample weight and density are determined at a given temperature (e.g., 15.6° C.), for example, by a method known by one of ordinary skill in the art. Liquid sample injection is accomplished with an auto sampler (e.g., Agilent 7683 B available from Agilent Technologies, Inc.). Components of the sample are identified by retention time, and the sample composition is calculated by gas chromatograph 102 utilizing a modified version (i.e. External Standard Quantification and grouping by pseudocomponents) of GPA Standard 2186-02 ("Method for the Extended Analysis of Hydrocarbon Liquid Mixtures Containing Nitrogen and Carbon Dioxide by Temperature Programmed Gas Chromatography," Revised and Adopted as a Standard 2002, Gas Processors Association), which is incorporated by reference herein. Components of the sample, including C1-C35 and the non-elution portion (C36+) total 100 wt %, with hydrocarbons eluting after n-pentane grouped and quantified as pseudo components, with the exception of a number of cyclic and aromatic compounds. FIG. 4 depicts a sample liquid chromatogram (some peaks labeled) obtained from analysis system 100.

Figure 5:
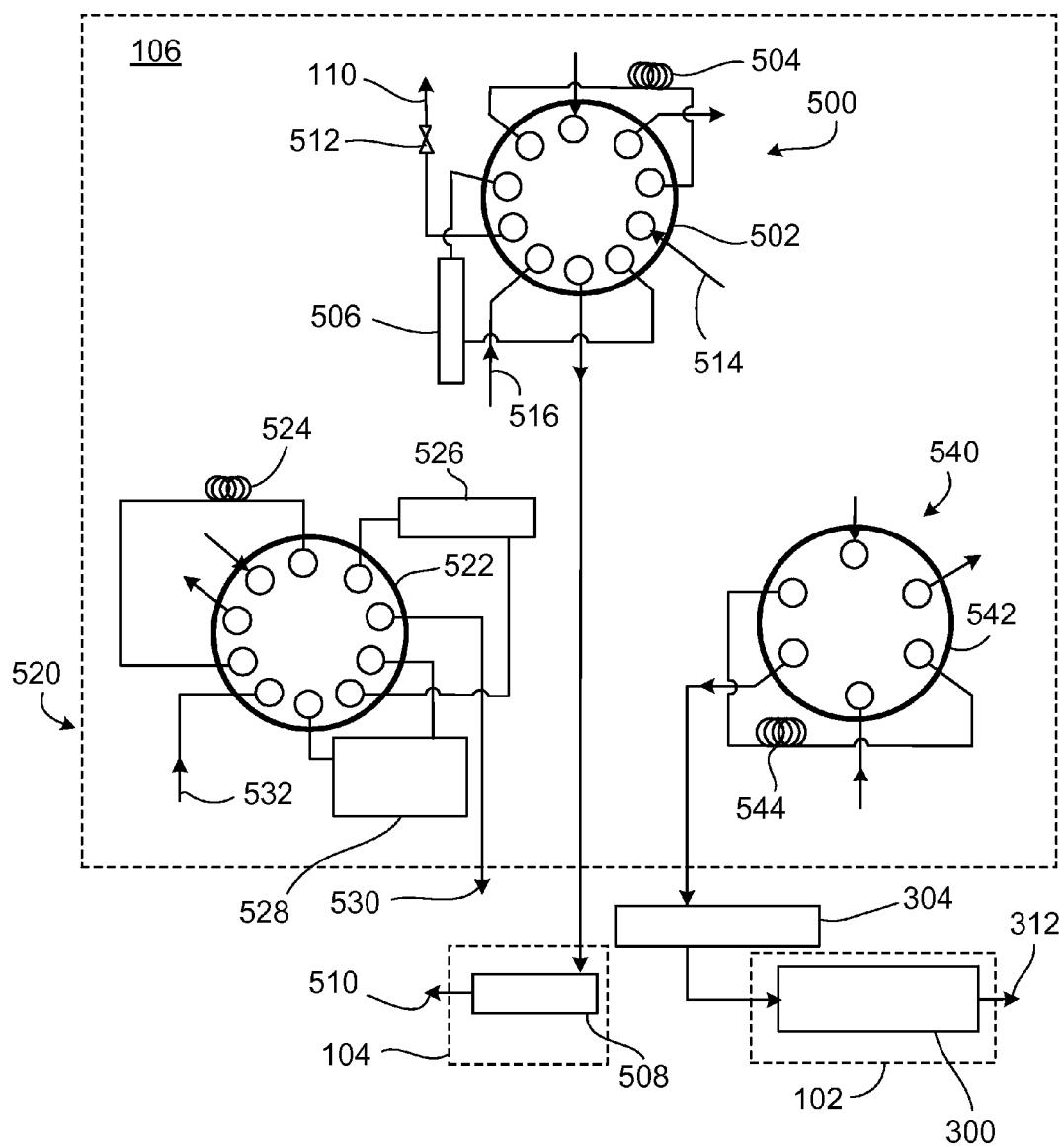
FIG. 5 depicts analytical subsystems in the isothermal oven of an analysis system.

Analysis system 100 includes three analytical subsystems for analysis of gas samples (e.g., from gasometer 238 of flash apparatus 104), including detection and quantification of C1 through C5, fixed gases (e.g., He or $H_2$, $N_2$, $O_2$, CO, and the like), and extended natural gas analysis (e.g., C6 through C20). The analytical subsystems are in conformance with published methods GPA 2261 ("Analysis for Natural gas and Similar Gaseous Mixtures by Gas Chromatography," Revised 2000, Gas Processors Association), which is incorporated by reference herein, and GPA 2286. As depicted in FIG. 5, portions of these analytical subsystems are housed in isothermal oven 106.

Analytical subsystem 500 is used for detection and quantification of fixed gases, including the carrier gas ($H_2$ or He, depending on carrier gas selection), $O_2$, $N_2$, and the like. As depicted, analytical subsystem 500 includes ten-port valve 502, available from Valco Instrument Co. Inc., sample loop 504, pre-column 506, molecular sieve analytical column 508, thermal conductivity detector 510, and flow controller 512. Pre-column 506 is a porous polymer column, and molecular sieve analytical column 508 is connected to thermal conductivity detector 510. Valve 502 is configured in a back flush to vent mode, which allows for components other than the carrier gas (e.g., hydrogen or helium), helium, oxygen, nitrogen, and methane to be isolated and back flushed to vent. The carrier gas facilitates the separation of helium, oxygen, nitrogen, and methane, which are eluted as individual distinct peaks. Molecular sieve analytical column 508 can be proximate (e.g., wrapped around) gasometer 238, whose temperature is controlled by temperature controller 244 located in flash apparatus 104. The temperature of transfer lines to and from molecular sieve analytical column 508 and thermal conductivity detector 510 are routed proximate to heated zones (e.g., injector 112, thermal conductivity detector 510, and external oven 106) to inhibit or prevent condensation of hydrocarbon gases.

Figure 6A:
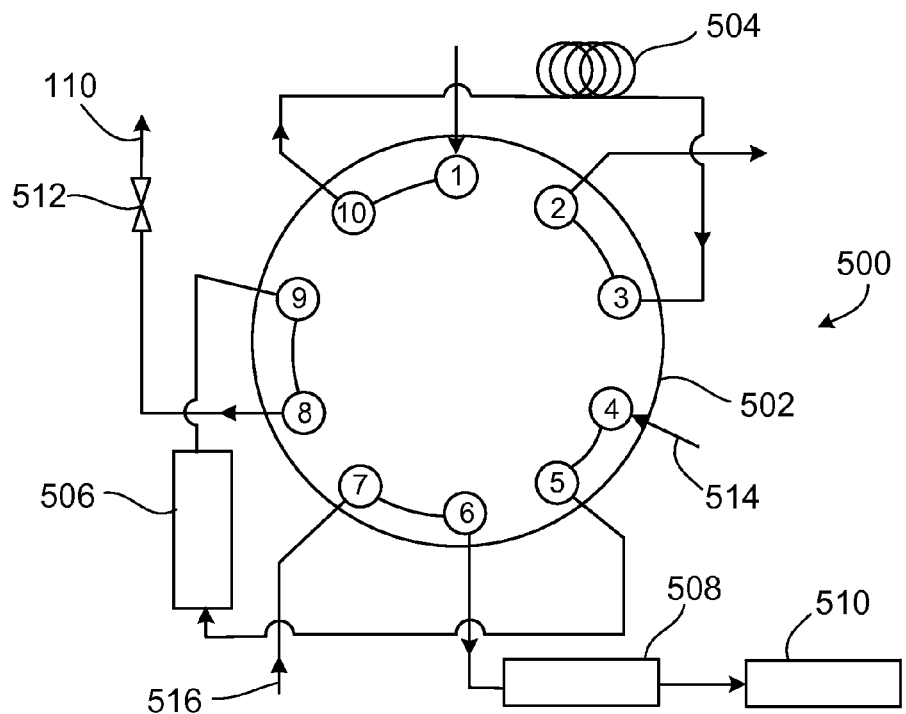
FIGS. 6A and 6B are schematics of a first analytical subsystem depicted in FIG. 5.

As depicted in FIG. 6A, valve 502 is initially switched "OFF" to fill sample loop 504. To fill sample loop 504, sample gas enters valve 502 through port 1, exits through port 10 to fill sample loop 504, enters the valve again through port 3, and exits through port 2. While sample loop 504 is filling, the rest of the subsystem is supplied with carrier gas to provide or maintain carrier flow during analysis. The carrier gases that flow through and pressurize the columns housed in the isothermal oven are controlled by gas chromatograph 102. First electronic pressure control 514 in gas chromatograph 102 controls the flow of carrier gas to back flush pre-column 506 and controls the primary flow for analytical subsystem 500. Carrier gas from first electronic pressure control 514 enters valve 502 through port 4, exits through port 5 to flush pre-column 506, enters the valve again through port 9, exits through port 8, and flows through flow controller 512 before exiting through gas inlet/outlet 110. Second electronic pressure control 516 in gas chromatograph 102 controls the flow of carrier gas to molecular sieve analytical column 508 and on to thermal conductivity detector 510. Carrier gas from second electronic pressure control 516 enters valve 502 through port 7, exits through port 6, flowing through molecular sieve analytical column 508, and then exits through thermal conductivity detector 510.

Figure 6B:
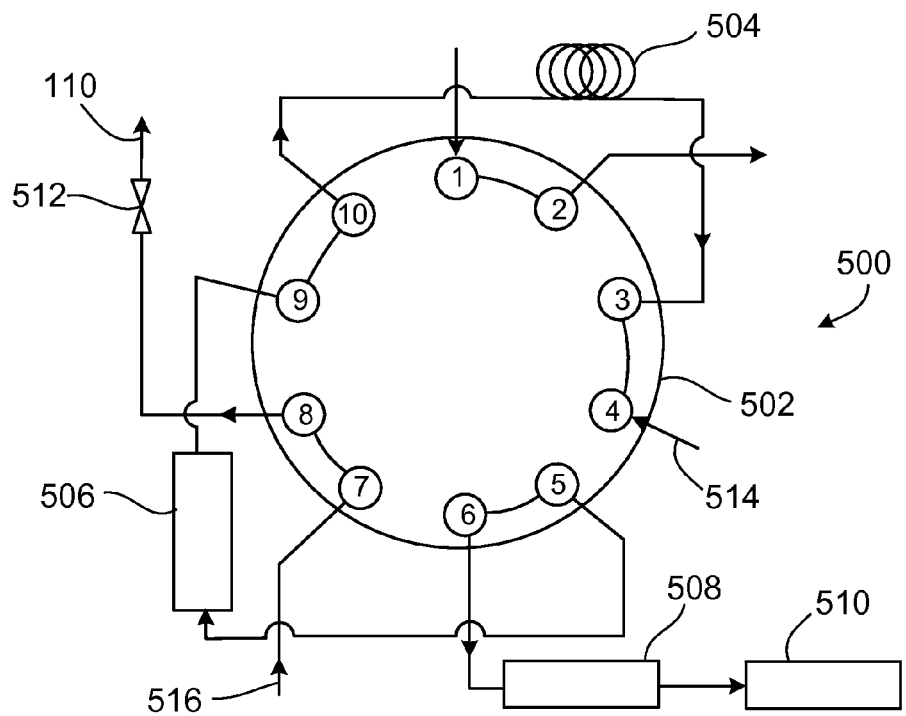
Figure 7:
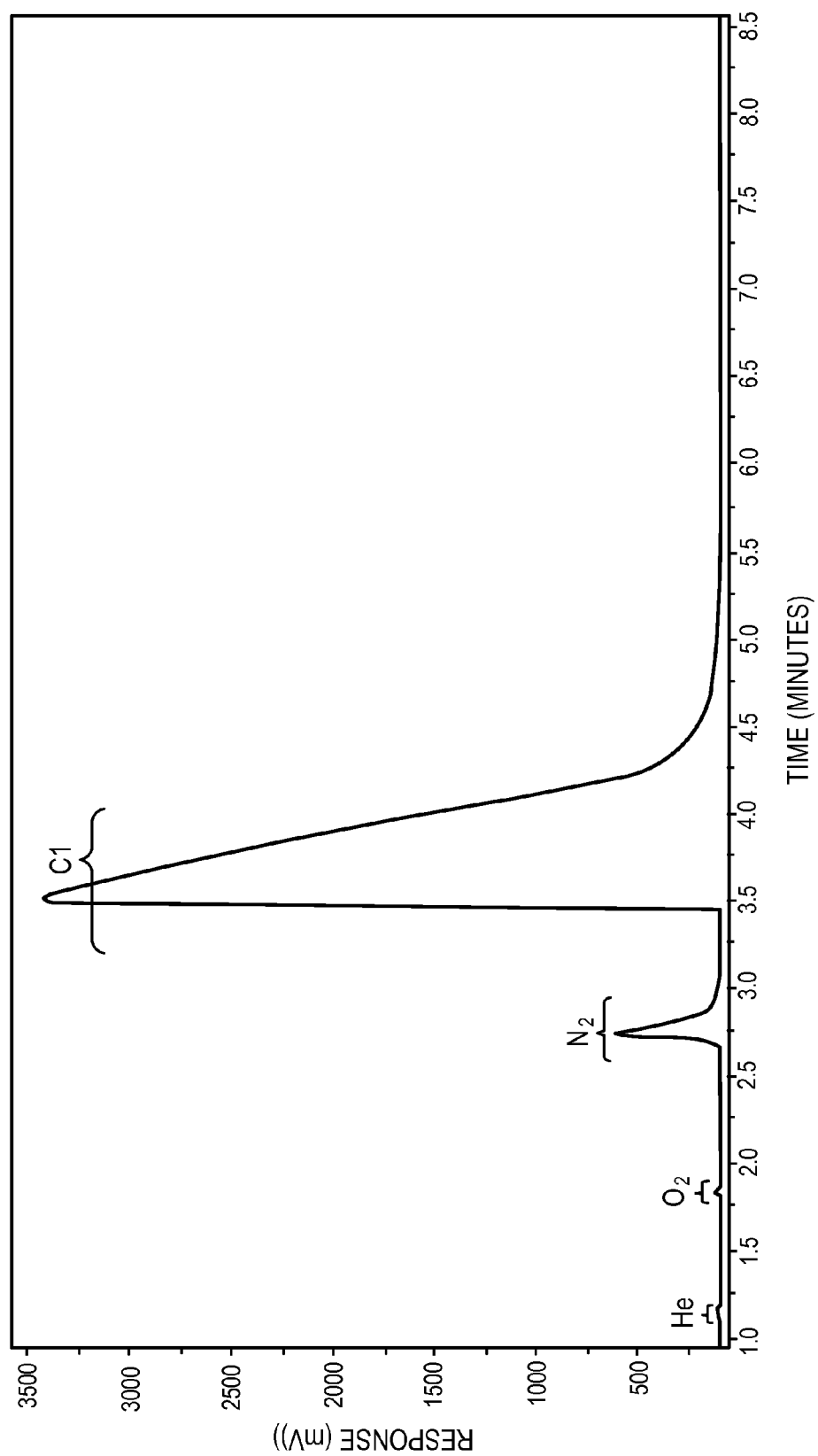
FIG. 7 depicts a sample chromatograph from the analytical subsystem depicted in FIGS. 6A and 6B.

When analysis system 100 is engaged to run a gas sample, valve 502 is switched to "ON," as depicted in FIG. 6B. Carrier gas from first electronic pressure control 514 enters port 4 of valve 502, exits through port 3, and pushes the sample through sample loop 504 and into port 10. The sample plus carrier gas then exits valve 502 through port 9, flows through pre-column 506, enters the valve through port 5, exits through port 6, and flows through molecular sieve analytical column 508 to thermal conductivity detector 510. Pre-column 506 isolates components heavier than methane, and molecular sieve analytical column 508 isolates and separates helium, oxygen, nitrogen, and methane. After an experimentally determined elapsed time (e.g., 0.1 min to 10 min, or 1.3 min to 1.7 min), valve 502 is switched "OFF" to allow the heavier components trapped in pre-column 506 column to vent and the components trapped in the molecular sieve analytical column 508 to run through thermal conductivity detector 510. FIG. 7 shows a sample chromatograph (major peaks labeled) from analytical subsystem 500.

Analytical subsystem 520 is used for detection and quantification of hydrocarbons including C1 to n-C5, as well as nitrogen and/or oxygen (e.g., air), carbon dioxide, hydrogen sulfide, and hydrocarbons larger than n-C5 (i.e., C6+). As depicted, analytical subsystem 520 includes ten-port valve 522, available from Valco Instrument Co. Inc., sample loop 524, pre-column 526, analytical column 528, and thermal conductivity detector 530. Columns 526 and 528 may be ⅛" SS nonpolar packed columns. In an example, pre-column 526 is 18 inches long and analytical column 528 is 30 feet long. Valve 522 is configured in a series reversal mode, which allows for components heavier than hexanes (C6+) to elute first as one conglomerate peak, followed by nitrogen and/or oxygen (e.g., air) methane, carbon dioxide, ethane, hydrogen sulfide, propane, i-C4, n-C4, i-C5, and n-C5, all as individual peaks.

Figure 8A:
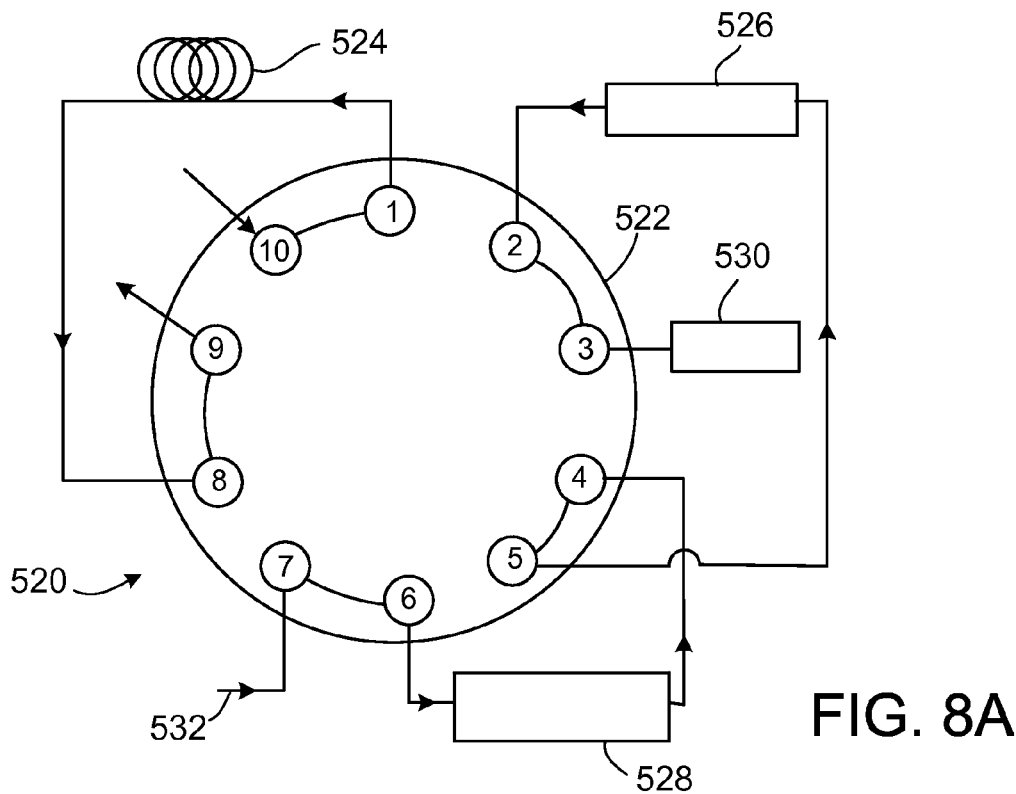
FIGS. 8A and 8B are schematics of a second analytical subsystem depicted in FIG. 5.

As depicted in FIG. 8A, valve 522 is initially switched to "OFF" to fill sample loop 524. To fill sample loop 524, sample gas enters valve 522 through port 10, exits through port 1 to fill sample loop 524, enters the valve through port 8, and exits through port 9. When sample loop 524 is filling, the rest of the subsystem is supplied with carrier gas to provide or maintain carrier gas flow. Carrier gas from third electronic pressure control 532 in gas chromatograph 102 enters valve 522 through port 7, exits through port 6, flows through analytical column 528, enters valve 522 through port 4, exits through port 5, flows through pre-column 526, enters the valve through port 2, exits the valve through port 3, and flows through thermal conductivity detector 530.

Figure 8B:
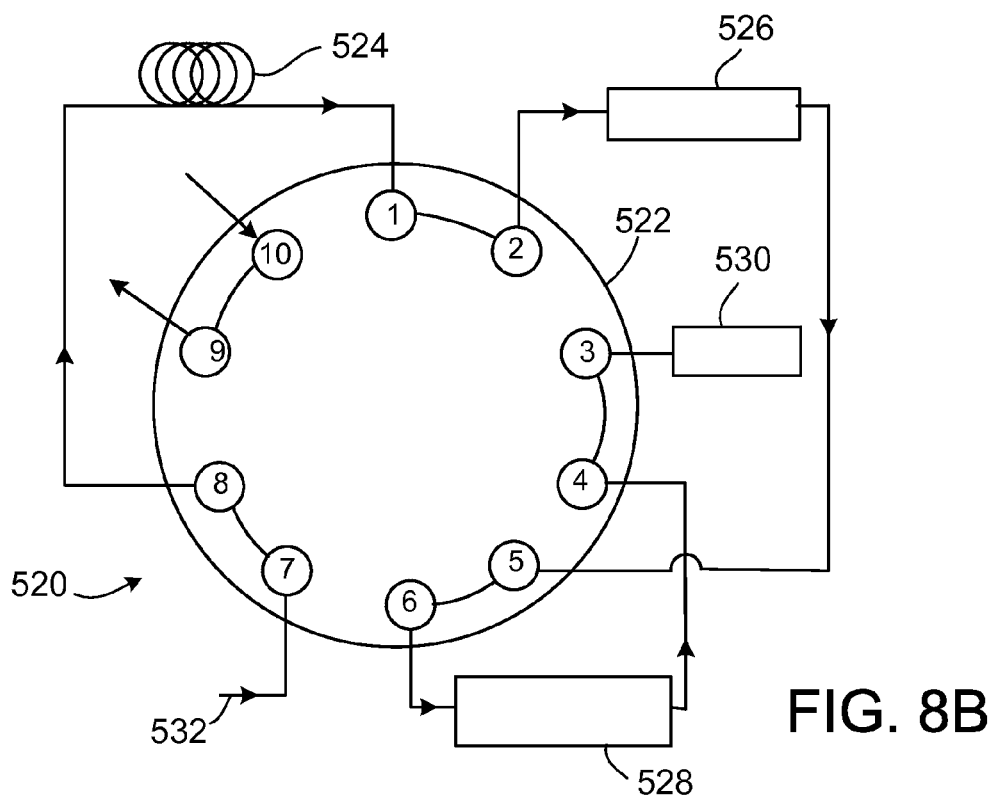
Figure 9:
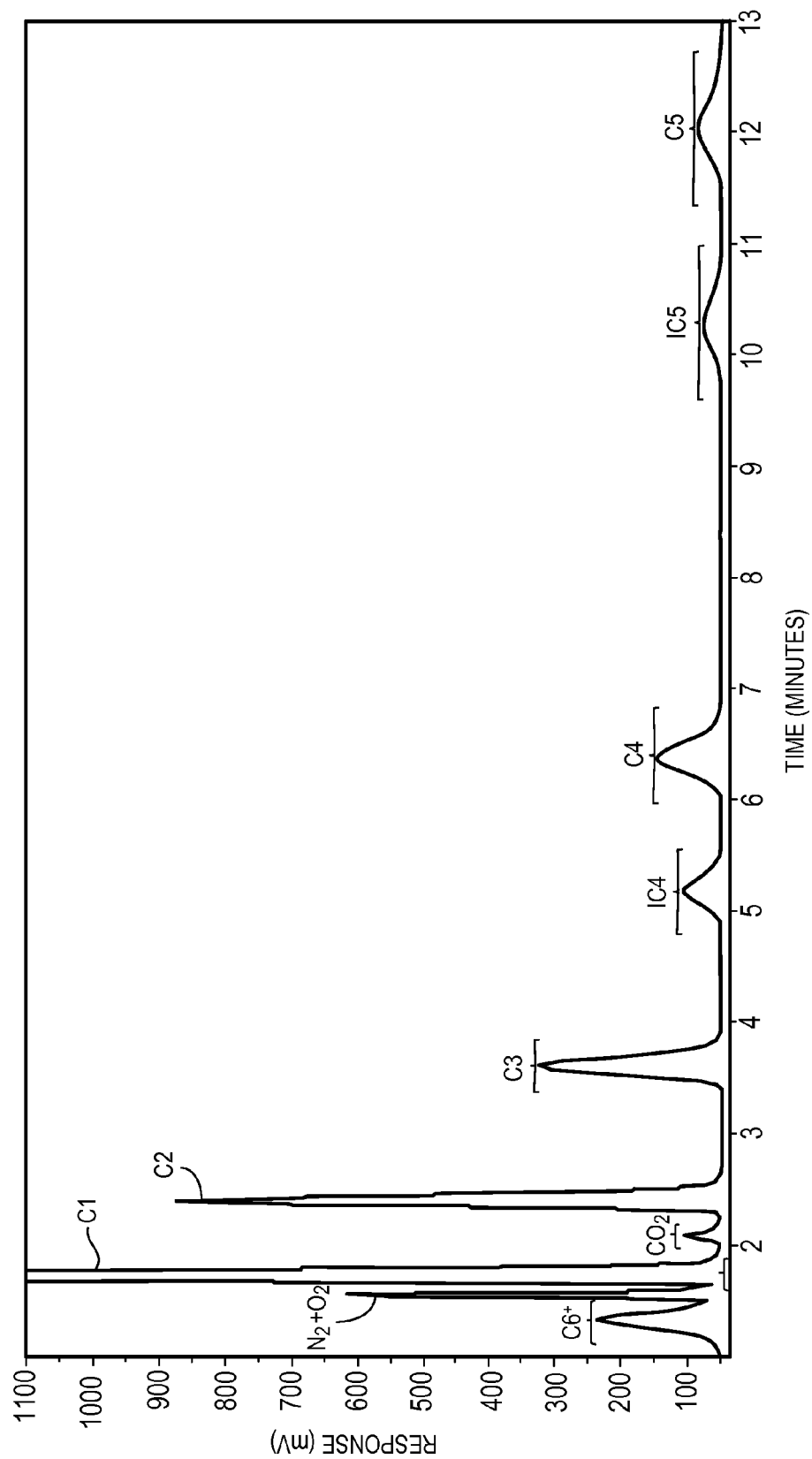
FIG. 9 depicts a sample chromatograph from the analytical subsystem depicted in FIGS. 8A and 8B.

When analysis system 100 is engaged to run a gas sample, valve 522 is switched to "ON," as depicted in FIG. 8B. With valve 522 switched to "ON," carrier gas from third electronic pressure control 532 flows into port 7 of valve 522, out port 8, flushes the sample through sample loop 524 and into valve 522 through port 1, out through port 2, and into pre-column 526. From pre-column 526, the sample flows into valve 522 through port 5, out through port 6, through analytical column 528, into valve 522 through port 4, out through port 3, and into thermal conductivity detector 530. Pre-column 526 traps the C6+ components, and analytical column 528 catches and separates components lighter than C6. At an experimentally determined elapsed time (e.g., 0.1 min to 10 min, or 0.7 min to 1.0 min), valve 522 is switched to "OFF" to allow the C6+ components to elute first as a conglomerate peak followed by the rest of the individually separated C1-C5 components through thermal conductivity detector 530. FIG. 9 shows a sample chromatograph (major peaks labeled) from analytical subsystem 520.

Analytical subsystem 540 includes six-port valve 542, available from Valco Instrument Co. Inc., sample loop 544, gas analytical column 300, four-port valve 308, and flame ionization detector 312. Gas analytical column 300 (in gas chromatograph 102) separates hydrocarbons ranging from methane (C1) to eicosane (C20). Components eluting after normal pentane (i.e., C6, C7, C8, etc.) are grouped as "pseudo" components, with the exception of user selected aromatics and isomers.

Figure 10A:
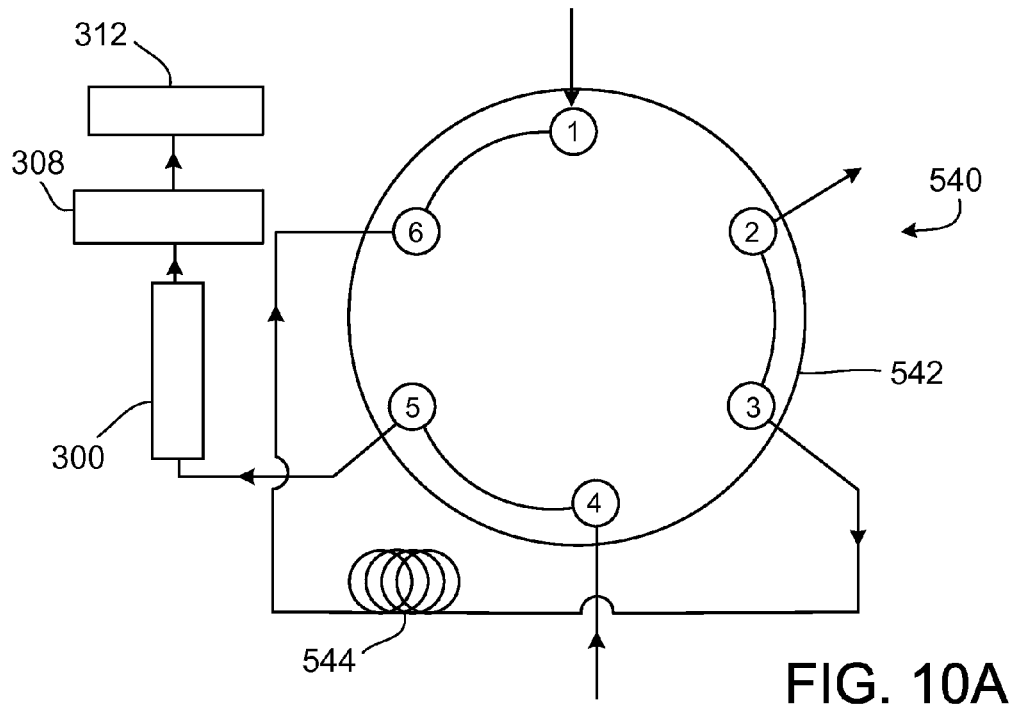
FIGS. 10A and 10B are schematics of a third analytical subsystem depicted in FIG. 5.
Figure 10B:
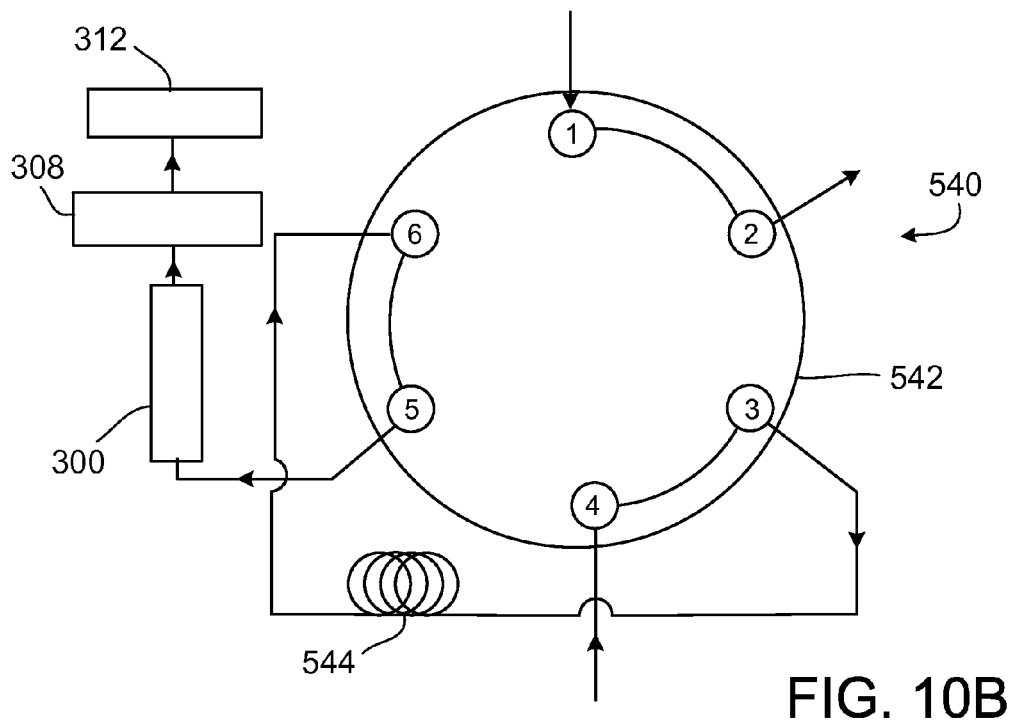
Figure 11:
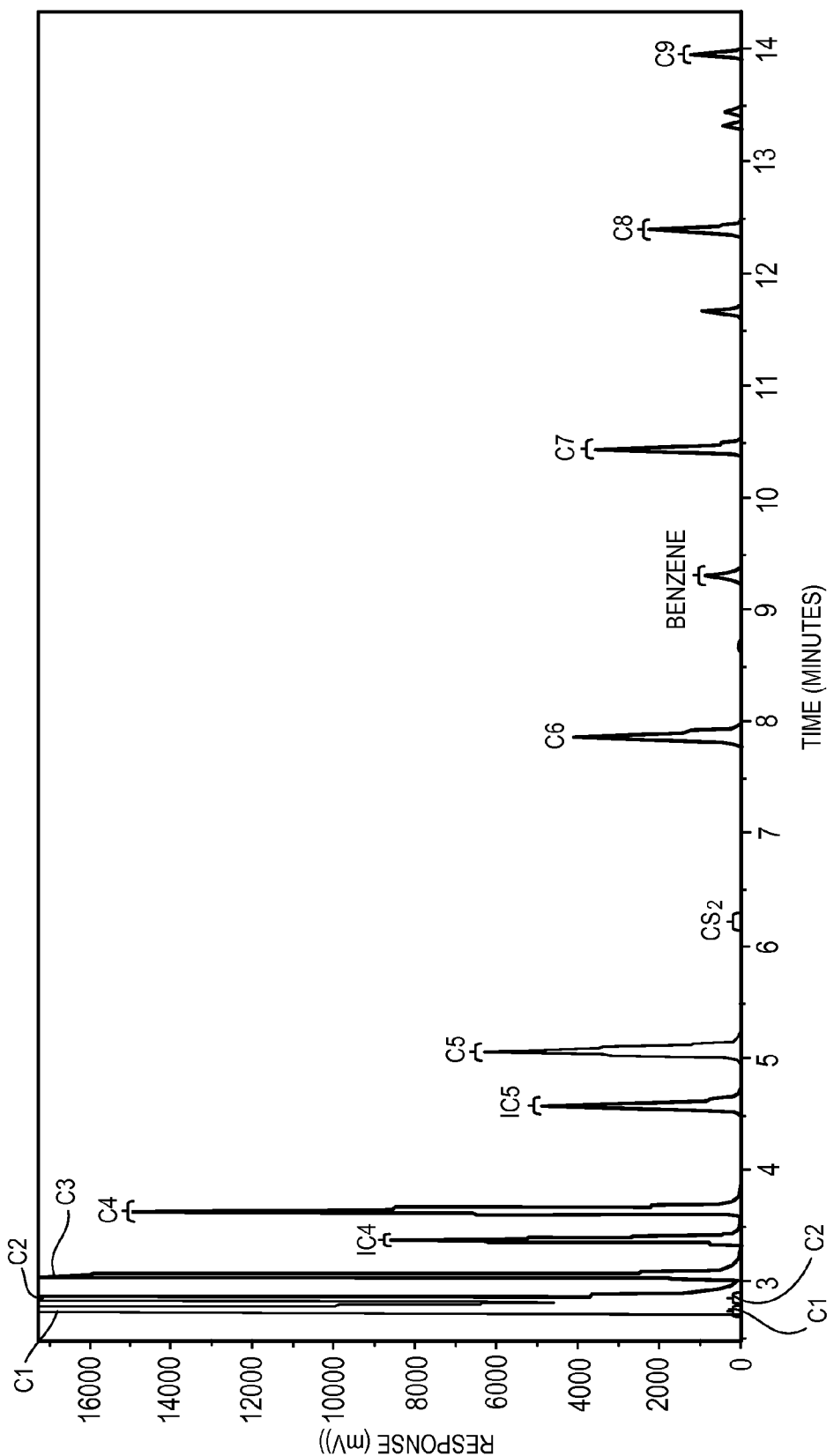
FIG. 11 depicts a sample chromatograph from the analytical subsystem depicted in FIGS. 10A and 10B.

Valve 542 is initially switched to "OFF," as depicted in FIG. 10A, to fill sample loop 544. The gaseous sample enters port 1 of valve 542, exits through port 6, fills sample loop 544, enters valve 542 through port 3, and exits through port 2. When sample loop 544 is filling, the rest of the subsystem is supplied with carrier gas in preparation for the start of the analysis process. Carrier gas from the front inlet 112 in gas chromatograph 102 enters valve 542 through port 4, exits valve 542 through port 5, flows through gas analytical column 300 and valve 308, then exits through flame ionization detector 312. When analysis system 100 is engaged to run a gas sample, valve 542 is switched to "ON," as depicted in FIG. 10B. Carrier gas enters valve 542 through port 4, exits the valve through port 3, forces the sample through sample loop 544 and into valve 542 through port 6, out of valve 542 through port 5, and into gas analytical column 300. After passing through gas analytical column 300, the sample moves through valve 308 and into flame ionization detector 312. FIG. 11 shows a sample chromatograph from analytical subsystem 540.

Isothermal oven 106 (available, for example, from Varian, Inc., now Agilent Technologies) houses valves 502, 522, and 542 as well as columns 506, 526, and 528. The temperature of isothermal oven 106 is controlled by temperature controller 116 proximate the top of gas chromatograph 102. Temperature controller 118 controls the temperature of transfer sample transfer line 322 from gas inlet 110 to an external sample source as in the case of sampling from a stainless steel sample cylinder or gas bag. All transfer lines in analysis system 100 are housed in the system (e.g., in flash apparatus 104, in gas chromatograph 102, in isothermal oven 106, etc.), and are heated such that formation of cold spots is avoided. Thus, the gaseous components are inhibited from condensing in the transfer lines.

Valves 502, 522, and 542 are linked to allow constant-volume sample loops coupled to these valves to be filled in series. As depicted in FIG. 12, a sample from flash apparatus 104 enters valve 502 through port 2. After filling sample loop 504, the gas flows out port 2 of valve 502 and enters port 1 of valve 542. After filling sample loop 544, the gas flows out of port 2 of valve 542 and enters port 10 of valve 522. After filling sample loop 524, the gas flows out of port 9 of valve 522 and exits the system through gas inlet/outlet 110. When dealing with samples containing poisonous or toxic components (e.g., hydrogen sulfide), a line can be run from gas inlet/outlet 110 through scrubbing solution 1300, as depicted in FIG. 13, to remove the poisonous or toxic components from the vented gas. In some cases, as depicted in FIG. 14, gas from gas inlet/outlet 110 can be bubbled through solution 1400 to sequester a known component, and the solution can be titrated using burette 1402.

While sample loops 504, 524, and 544 are filling, the rest of analytical subsystems 500, 520, and 540 are purged with carrier gas. After sample loops are filled and the vapor has reached an equilibrium temperature and pressure, valves 502, 522, and 542 are switched from "OFF" to "ON" simultaneously, and carrier gas forces the sample vapor through the sample loops and into thermal conductivity detector 510, thermal conductivity detector 530, and gas analytical column 300, respectively, for detection and quantitative determination. Vapor sample data from analytical subsystems 500, 520, and 540 are acquired by data acquisition system 122 and are manipulated by microprocessor 124. The vapor sample data can be combined with liquid sample data obtained as described herein with reference to FIGS. 3 and 4 to yield the composition of the sample (e.g., live fluid) from pycnometer 200.

In some cases, gas inlet/outlet 110 can be used to back flow gas through the sample lines and into gasometer 238. In an example, a carrier gas source coupled to gas inlet/outlet 110 is used to flush sample or atmospheric air from analysis system 100. The carrier gas flows into valve 522, from valve 522 to valve 542, from valve 542 to valve 502, and from valve 502 to gasometer 238 in flash apparatus 104.

Microprocessor 124, depicted in FIG. 1A, allows automated control of analysis system 100, including recognizing fluid equilibrium, accurately setting and reading temperature, pressure, and volume devices, all of which can affect the reliability of the data generated. Automated control can be implemented using hardware, software, or both. Software can be configured to run testing protocols with as little operator influence as possible and can fully monitor and control pressure, volumetrics, and temperature. In some cases, software is configured to control (e.g., maintain or change) the sample volume while pushing gas, liquid, and/or solid from, for example, flash apparatus 104 to gas chromatograph 102. During this process, pressure, volume, temperature, and chromatographic data are logged, allowing calculation of the desired properties (e.g., PVT properties). In an example, valve 252 is operated automatically, such that a fluid sample from pycnometer 200 undergoes flash vaporization and the vapor sample flows directly from flash apparatus 104 to gas chromatograph 102. Valves 502, 522, and 542 may also be operated automatically, such that a vapor sample from flash apparatus 104 fills sample loops 504, 524, and 544 in series, and flow of the vapor sample from the sample loops to flame ionization detector 312 and thermal conductivity detectors 510 and 530 is initiated substantially simultaneously.

Further modifications and alternative embodiments of various aspects will be apparent to those skilled in the art in view of this description. Accordingly, this description is to be construed as illustrative only. It is to be understood that the forms depicted and described herein are to be taken as examples of embodiments. Elements and materials may be substituted for those illustrated and described herein, parts and processes may be reversed, and certain features may be utilized independently, all as would be apparent to one skilled in the art after having the benefit of this description. Changes may be made in the elements described herein without departing from the spirit and scope as described in the following claims.

What is claimed is:

1. An analysis system comprising:
a common housing comprising:
   a flash apparatus configured to partially vaporize a pressurized reservoir fluid by reduction in pressure across a valve to yield a vaporized gas and a reservoir liquid;
   a first chromatography subsystem comprising a first chromatography column and a first sample loop, the first sample loop fluidly coupled to the flash apparatus and configured to receive the vaporized gas from the flash apparatus;
   a second chromatography subsystem comprising a second chromatography column and a second sample loop, the second sample loop fluidly coupled to the first sample loop and configured to receive the vaporized gas from the flash apparatus via the first sample loop, wherein the first chromatography column of the first chromatography subsystem and second chromatography column of the second chromatography subsystem are configured to be actuated simultaneously to detect components in the pressurized reservoir fluid;
   a single data acquisition system coupled to the first chromatography subsystem, the second chromatography subsystem, and the flash apparatus, wherein the single data acquisition system is configured to acquire data related to the composition of the pressurized reservoir fluid provided to the flash apparatus; and
   a microprocessor coupled to the data acquisition system, wherein the microprocessor is operable to assess a gas to oil ratio of the pressurized reservoir fluid provided to the flash apparatus based on the data acquired by the data acquisition system.

2. The analysis system of claim 1, wherein the first chromatography subsystem is configured to detect fixed gases.

3. The analysis system of claim 1, wherein the second chromatography subsystem is configured to detect C1 to C5 hydrocarbons.

4. The analysis system of claim 1, wherein the housing further comprises a third chromatography subsystem, and the third chromatography subsystem comprises a chromatography column configured to detect C1 to C20 hydrocarbons.

5. The analysis system of claim 4, wherein the third chromatography subsystem comprises a flame ionization detector.

6. The analysis system of claim 5, further comprising:
a gas analytical capillary column;
a liquid analytical capillary column; and
a selector valve,
   wherein the gas analytical capillary column and the liquid analytical capillary column are coupled to the flame ionization detector via the selector valve.

7. The analysis system of claim 6, wherein the third chromatography subsystem comprises the gas analytical capillary column.

8. The analysis system of claim 1, wherein the first chromatography subsystem comprises a first thermal conductivity detector and the second chromatography subsystem comprises a second thermal conductivity detector.

9. The analysis system of claim 1, further comprising a conduit configured to transport vaporized gas from the flash apparatus to the first chromatography subsystem, wherein a temperature of the conduit is controlled using available heat in the analysis system.

10. The analysis system of claim 1, wherein the flash apparatus is configured to partially vaporize the pressurized reservoir fluid to yield free water along with the vaporized gas and the reservoir liquid.

11. The analysis system of claim 1, wherein the flash apparatus is configured to partially vaporize the pressurized reservoir fluid to yield an equilibrated reservoir liquid.

12. A method comprising:
partially vaporizing a pressurized reservoir fluid to form a vaporized gas and a reservoir liquid;
inhibiting condensation of the vaporized gas, wherein inhibiting condensation of the vaporized gas comprises heating the vaporized gas;
automatically providing a single sample of the heated vaporized gas to a first sample loop of a first chromatography subsystem and a second sample loop of a second chromatography subsystem in series and actuating a first chromatography column of the first chromatography subsystem and a second chromatography column of the second chromatography subsystem simultaneously to detect components in the heated vaporized gas;
acquiring data related to the composition of the heated vaporized gas from the two chromatography subsystems with a single data acquisition system;
quantifying the composition of the reservoir liquid based on the data acquired by the single data acquisition system; and
assessing a weight ratio of the vaporized gas to the reservoir liquid.

13. The method of claim 12, further comprising automatically providing a portion of the single sample of the vaporized gas to a third chromatography subsystem in series with the two chromatography subsystems.

14. The method of claim 12, further comprising:
providing a portion of the reservoir liquid to a third chromatography subsystem;
acquiring data related to the composition of the reservoir liquid from the third chromatography subsystem with the single data acquisition system;
combining the data related to the composition of the reservoir liquid and the data related to the composition of the vaporized gas; and
quantifying the composition of the pressurized reservoir fluid based on the data acquired by the single data acquisition system.

15. The method of claim 12, wherein inhibiting condensation of the vaporized gas comprises heating the vaporized gas with available heat.

* * * * *